(12) United States Patent
Dirauf et al.

(10) Patent No.: US 9,737,270 B2
(45) Date of Patent: Aug. 22, 2017

(54) COLLISION SENSOR DEVICE FOR A MEDICAL APPARATUS, AND MEDICAL APPARATUS

(71) Applicants: Franz Dirauf, Ebensfeld (DE); Verena Schmidt, Erbendorf (DE)

(72) Inventors: Franz Dirauf, Ebensfeld (DE); Verena Schmidt, Erbendorf (DE)

(73) Assignee: Siemens Aktiengesellschaft, München (DE)

( * ) Notice: Subject to any disclaimer, the term of this patent is extended or adjusted under 35 U.S.C. 154(b) by 165 days.

(21) Appl. No.: 14/527,305

(22) Filed: Oct. 29, 2014

(65) Prior Publication Data
US 2015/0117615 A1   Apr. 30, 2015

(30) Foreign Application Priority Data
Oct. 30, 2013   (DE) .................. 10 2013 222 115

(51) Int. Cl.
*A61B 6/10* (2006.01)
*H01L 23/64* (2006.01)
(Continued)

(52) U.S. Cl.
CPC .............. *A61B 6/102* (2013.01); *A61B 6/547* (2013.01); *H01L 23/64* (2013.01); *H01L 41/125* (2013.01);
(Continued)

(58) Field of Classification Search
CPC .... A61B 6/00; A61B 6/02; A61B 6/03; A61B 6/032; A61B 6/035; A61B 6/10; A61B 6/102; A61B 6/105; A61B 6/44; A61B 6/4429; A61B 6/4476; A61B 6/54; A61B 6/547; H01L 23/00; H01L 23/02;
(Continued)

(56) References Cited

U.S. PATENT DOCUMENTS 5,060,527 A * 10/1991 Burgess .................. G01L 1/205
                                                            338/47
5,651,044 A *  7/1997 Klotz, Jr. ................. H05G 1/26
                                                            378/117
(Continued)

FOREIGN PATENT DOCUMENTS

CN         101232056 A      7/2008
CN         202903205 U      4/2013
(Continued)

OTHER PUBLICATIONS

German Office Action for German Application No. 10 2013 222 115.0, mailed Jul. 8, 2014, with English Translation.
(Continued)

*Primary Examiner* — Anastasia Midkiff
(74) *Attorney, Agent, or Firm* — Lempia Summerfield Katz LLC

(57) ABSTRACT

A collision sensor device for a medical apparatus includes a sensor structure having a first sensor and a second sensor that are separated by a spacer layer, at least one crumple layer that adjoins one of the first sensor and the second sensor and is configured to provide a run-on path, and an outer surface layer provided on a side facing away from the medical apparatus in an installed state of the collision sensor device.

20 Claims, 2 Drawing Sheets

(51) Int. Cl.

| | | |
|---|---|---|
| *H01L 41/12* | (2006.01) | |
| *A61B 6/00* | (2006.01) | |
| H01L 23/58 | (2006.01) | |
| H01L 29/84 | (2006.01) | |
| H01L 23/18 | (2006.01) | |
| G05B 19/4061 | (2006.01) | |
| G01D 21/02 | (2006.01) | |

(52) U.S. Cl.
CPC ........... *A61B 6/4405* (2013.01); *A61B 6/4441* (2013.01); *G01D 21/02* (2013.01); *G05B 19/4061* (2013.01); *H01L 23/18* (2013.01); *H01L 23/585* (2013.01); *H01L 29/84* (2013.01)

(58) Field of Classification Search
CPC ......... H01L 23/16; H01L 23/18; H01L 23/24; H01L 23/28; H01L 23/29; H01L 23/293; H01L 23/31; H01L 23/3107; H01L 23/3121; H01L 23/52; H01L 23/522; H01L 23/5227; H01L 23/5228; H01L 23/58; H01L 23/585; H01L 23/64; H01L 23/642; H01L 23/645; H01L 23/647; H01L 29/66; H01L 29/66007; H01L 29/66075; H01L 29/66083; H01L 29/66166; H01L 29/66174; H01L 29/66181; H01L 29/66189; H01L 29/66196; H01L 29/84; H01L 41/12; H01L 41/125; H01L 41/20; H01L 41/47; H05G 1/00; H05G 1/02; H05G 1/08; H05G 1/26; H05G 1/54; G05B 19/00; G05B 19/02; G05B 19/18; G05B 19/19; G05B 19/406; G05B 19/4061; G05B 2219/24145; G05B 2219/37237; G05B 2219/37622; G05B 2219/37623; G05B 2219/37631; G05B 2219/39082; G05B 2219/39088; G05B 2219/39091; G05B 2219/39135; G05B 2219/40317; G05B 2219/403

See application file for complete search history.

(56) References Cited

U.S. PATENT DOCUMENTS

| | | |
|---|---|---|
| 5,917,180 A | 6/1999 | Reimer et al. |
| 2004/0257744 A1* | 12/2004 | Bushko .................. A61B 6/102 361/179 |
| 2006/0097734 A1* | 5/2006 | Roziere .................. A61B 6/102 324/662 |
| 2007/0193380 A1 | 8/2007 | Klein et al. |
| 2007/0200396 A1* | 8/2007 | Baumann ............. A61B 6/0457 297/135 |
| 2010/0061509 A1 | 3/2010 | D'Ambrosio et al. |
| 2012/0104904 A1 | 5/2012 | Abiko et al. |
| 2013/0204157 A1 | 8/2013 | Clark et al. |
| 2013/0218050 A1 | 8/2013 | Eichhorn et al. |
| 2014/0090488 A1* | 4/2014 | Taylor ...................... G01L 1/18 73/862.625 |

FOREIGN PATENT DOCUMENTS

| | | |
|---|---|---|
| CN | 203132562 U | 8/2013 |
| DE | 69808293 | 5/2003 |
| DE | 10201221379 A1 | 8/2013 |
| EP | 0462295 A1 | 12/1991 |
| EP | 2502562 A1 | 9/2012 |

OTHER PUBLICATIONS

Chinese office Action for related Chinese Application No. 201410535021.3 dated Jul. 5, 2016 with English Translation.

\* cited by examiner

COLLISION SENSOR DEVICE FOR A MEDICAL APPARATUS, AND MEDICAL APPARATUS

RELATED APPLICATIONS

This application claims the benefit of German Patent Application No. DE 102013222115.0, filed Oct. 30, 2013. The entire contents of the priority document are hereby incorporated herein by reference.

TECHNICAL FIELD

The present teachings relate generally to a collision sensor device for a medical apparatus, to a medical apparatus, and to a medical apparatus having at least one such collision sensor device.

BACKGROUND

In medical apparatuses having at least one moving component, components of the apparatus may collide with one another or with persons coming into contact with the components. Therefore, collision sensors are used for the purpose of protecting people and machines. The collision sensors may detect contact between a part of the medical apparatus and other components of the medical apparatus or a person. Hazardous situations are identified by a control device of the medical apparatus, such that corresponding measures may be taken (e.g., stopping a movement of a movable component of the medical apparatus and/or the output of warnings).

The robustness and disinfectability of contact parts is oftentimes desirable in the field of medical apparatuses (e.g., including collision sensors).

Conventional collision sensors for measuring force, collision, and/or pressure record measured values only selectively and in a spatially limited manner (e.g., in the example of a load cell or a conventional pressure sensor). Collision sensor devices for two-dimensional detection have been used (e.g., safety mats and safety edges used in safety technology and tactile floors for detecting whether elderly people are lying on the floor). However, the sensor principles used do not satisfy the criteria for disinfectability and robustness of medical apparatuses.

SUMMARY AND DESCRIPTION

The scope of the present invention is defined solely by the appended claims, and is not affected to any degree by the statements within this summary.

The present embodiments may obviate one or more of the drawbacks or limitations in the related art. For example, in some embodiments, a flat collision sensor device for a medical apparatus is provided. The device may detect contact over a larger area and complies with other criteria in the field of medical technology.

In some embodiments, a collision sensor device for a medical apparatus is provided that has a multilayer, flat structure. The collision sensor device includes: a sensor structure having two sensors (e.g., a first sensor and a second sensor) that are separated by a spacer layer and are configured to provide separate measurement data; at least one crumple layer that adjoins a sensor and provides a run-on path; and an outer surface layer that is provided on a side that faces away from the medical apparatus in an installed state of the collision sensor device.

Modern sensor technologies allow the formation of flat sensors (e.g., textile layers) that may be combined in a layer structure with a surface layer to fulfill medical criteria. A simple, flat collision sensor may be constructed in the manner of a "sandwich" by joining different materials (e.g., fabrics and materials) in different thicknesses in order to achieve different properties used in medical technology. The use of a surface layer may be used to satisfy criteria for disinfection, robustness, and optical appearance (e.g., color). A crumple layer provides run-on paths that in the event of a collision form a buffer before damage occurs. The buffer provides a reaction time such that a control device and/or a person warned by a warning may have time to react. The layers present in addition to the sensor structure may be used to satisfy criteria of the medical technology.

In summary, the use of a "sandwich" structure may be used for flexibly achieving the properties of tactile sensor devices (e.g., collision sensor devices) for collision protection in medical technology.

Flat collision sensor devices of any desired area may be implemented. By way of example, the area may range from 5×5 cm up to the lining of entire components (e.g., robot arms) of the medical apparatus. The height of the layer structure may be smaller than other dimensions (e.g., circumference), since the layer structure is a flat device. For example, the circumference of the surface of the layer structure may exceed 50 times the height. In some embodiments, the overall height of the layers may range from 5 mm to 5 cm, depending mainly on the height of the crumple layer.

The sensor structure may have, for example, a thickness of 2 mm to 8 mm. The greatest proportion of the thickness is due to the spacer layer. However, it is to be understood that other thicknesses and sizes may also be used depending on the application.

Two sensors that operate separately may be separated by a spacer layer that avoids mutual interference in the measurement. The spacer layer may also achieve a run-on path if the two sensors are used for staged triggering of measures in the event of a collision. Thus, there may be advantages when using different sensors that are based on different sensor principles. Furthermore, there is redundancy of the overall measurement. The sensor data from the sensors allow a mutual plausibility check and/or detection of a collision even when only one of the sensors detects an event (e.g., since the other measurement principle is not affected). On the other hand, the two sensors may also operate according to the same sensor principle and allow staged triggering if the spacer layer provides a defined run-on path. Furthermore, the integrity of the entire sensor system may be checked. A first fault may be reliably detected by independent sensors with a continuous force-dependent signal output. The safety criteria for medical devices may be thus fulfilled.

In the staged triggering, a control device of the medical apparatus may determine that the sensor closer to the surface layer responds first. In this example, a first triggering stage may be determined wherein, for example, a warning is output and/or the movement of an automatically moved component of the medical apparatus is slowed down. If the second sensor also detects an event after a period of time, a second triggering stage is reached wherein an automatic movement of a component may be definitively stopped and/or an intensified warning may be output (e.g., if the control device does not influence the collision process).

In some embodiments, the two sensors are based on different sensor principles. The two sensors may be based on different sensor principles when staged triggering is intended since the redundancy remains. The individual sensors may be subdivided into sublayers (e.g., an upper conductive sublayer, an intermediate layer, and a lower conductive sublayer) in order to achieve a separate sensor operating according to the capacitive, resistive, or inductive sensor principle in a sensor layer.

Even if the sensor structure contains at least three layers, a flat implementation may be used. The collision sensor device remains flat enough to be arranged on the corresponding components of the medical apparatus.

In some embodiments, the sensors are formed from a textile material. Different measurement principles may be used as the sensor principles. For example, a capacitive and/or a resistive and/or an inductive sensor principle, and/or a sensor principle based on light scattering in at least one cavity in the sensors (e.g., a cavity having a variable size depending on a pressure acting on the collision sensor device), may be used. Textile materials may be used in the sensors for all of the above-described measurement principles. Conductive layers may be used in sensors based on capacitive, resistive, and inductive measurement principles. At least partially conductive textile materials may include, for example, threads coated with conductive material (e.g., carbon nanotubes), individual inserted threads, and the like. Conductive non-wovens may also be used. The use of embroidered materials wherein the embroidery is carried out with a conductive material facilitates achieving a spatially resolved sensor in a simple manner. A type of matrix structure is achieved in the corresponding sensor. However, other at least partially conductive textile materials may be used. For example, elastic and/or textile materials (e.g., those sold under the trade name KINOTEX) may be used for sensor principles based on light scattering in cavities, as described, for example in DE 698 08 293 T2. The use of textile materials for the sensors allows simple processing via textile processing methods, as further described below.

The spacer layer may be formed from a spacer fabric and/or a foam. Spacer fabrics include double-face textiles wherein spacer-connecting threads (e.g., pile threads) keep the outer surfaces at a distance. For the rest, foam may be used to achieve defined run-on paths or for elasticity properties.

In some embodiments, the sensor (or at least one of the sensors) formed by the sensor structure is configured for spatially resolved measurement. For sensor principles based on electrical or magnetic interactions, structured conductive layers may be implemented (e.g., to apply matrix structures that allow measured signals to be located). For sensors based on the sensor principle of light scattering in cavities, optical waveguides may be placed at different locations, such that a spatially resolved measurement may be achieved. The cavity structure may be configured accordingly.

The crumple layer (or one of the at least one crumple layer) may adjoin the sensor structure on a side of the sensor structure that faces the medical apparatus in the installed state. The sensitivity of the sensor structure to pressures is largely retained while, at the same time, a run-on path that may avoid injuries and/or damage is implemented downstream of the sensor. The crumple layer (or one of the at least one crumple layer) may adjoin the sensor structure on a side that faces away from the medical apparatus in the installed state, such that the sensor structure (e.g., the sensors) may be protected.

The crumple layer may include a spacer fabric or a foam. The crumple layer may have a thickness corresponding to a run-on path (e.g., a thickness of between 0.5 cm and 4 cm). Other thicknesses of crumple layers may also be used for run-on paths depending on the compression hardness of the material.

The surface layer may include a material that may be cleaned and/or disinfected (e.g., artificial leather) and/or have a thickness of 1 mm to 10 mm. Artificial leather is a robust material that may be cleaned and disinfected to fulfill the criteria of medical apparatuses. Other materials may also be used for the surface layer. For example, rubber-like surfaces made of plastic may be used as the surface layer (e.g., by coating and/or welding methods). Such surfaces likewise may have a high degree of robustness and disinfectability.

In some embodiments, all layers may be textile layers and/or layers that may be processed by textile connecting methods (e.g., lamination and/or coating), and/or be adhesively connected. The sandwich structure may be created by connecting the individual layers, and adhesively holding the layers together using textile industry methods (e.g., coating and lamination). Alternatively, in some embodiments, the layers may be connected by sewing and/or stitching. Overall, the collision sensor device may be produced in a simple and cost-effective manner. In some embodiments, foam (e.g., for the spacer layer and crumple layer) may be used to connect to additional layers using textile industry methods.

The collision sensor device also has reading components that are dependent on the sensor principle used. The reading components are used to pass the sensor data measured by the sensors to a suitable control device of the medical apparatus.

In addition to a collision sensor device, the present teachings also relate to a medical apparatus having at least one collision sensor device of a type described herein and a control device that evaluates sensor data from the at least one collision sensor device. All of the description provided above in relation to the collision sensor device may also be applied to a medical apparatus in accordance with the present teachings.

The medical apparatus may have at least one moving component. The at least one moving component may be provided with at least one collision sensor device. Since the collision sensor device is flat, at least one movable component of the medical apparatus may be lined with the collision sensor device. However, collision sensor devices may also be provided on non-moving components of the medical apparatus that may come into contact with other components and/or also objects outside the apparatus, (e.g., beds, chairs, and the like). Collision sensor devices may also be provided on components that may come into contact with a patient or other persons in an undesirable manner. The sensor of the collision sensor devices may be configured for spatially resolved measurement to provide a larger, more accurate information base in the control device that may carry out corresponding measures (e.g., the output of warnings and/or the changing of the movement control of movable components of the medical apparatus).

For a collision sensor device having two sensors separated by the spacer layer, the control device may be configured to evaluate the sensor data from the sensor closer to the surface layer (e.g., the first sensor or the second sensor) with regard to a first triggering stage, and to evaluate the sensor data from the other sensor with regard to a second triggering stage and/or to check the plausibility of the sensor data (e.g., if different sensor principles are used). For example, the movement of components may already be slowed down in a first triggering stage, while the components are completely stopped in the second triggering stage. Different warning stages may be used.

In some embodiments, the medical apparatus includes an image-recording device and/or other measuring device configured for recording data relating to the patient. The medical apparatus may be, for example, an x-ray device with a C-arm. The C-arm has a plurality of degrees of freedom that may result in a risk of collision. Medical apparatuses having at least one other movable component (e.g., a robot arm) may also include a collision sensor device in accordance with the present teachings.

DETAILED DESCRIPTION

Figure 1:
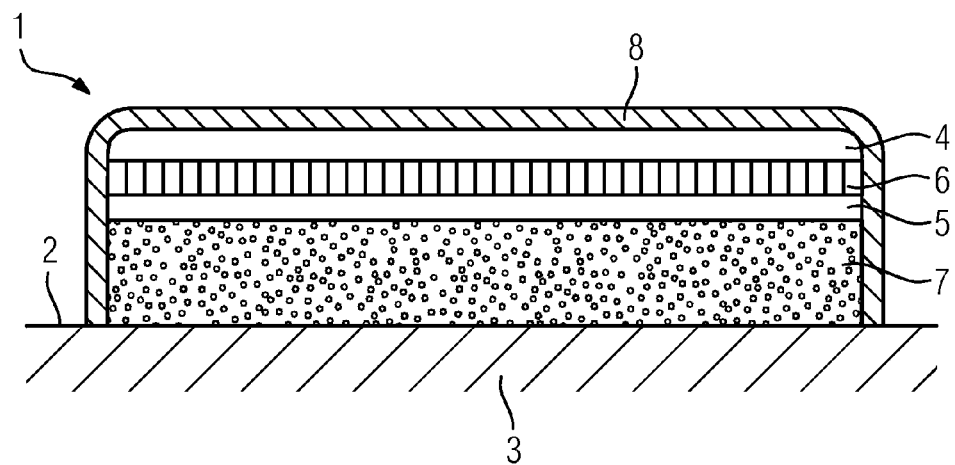
FIG. 1 shows a cross-sectional view of a first example of a collision sensor device.

FIG. 1 shows a cross-sectional view of an exemplary collision sensor device 1 in accordance with the present teachings. The collision sensor device 1 has already been applied to a surface 2 of a medical apparatus 3. For the sake of simplicity, reading components of the collision sensor device 1 that are provided for the purpose of reading are not shown in FIG. 1. The reading components may be present, depending on the sensor principle, in order to supply the sensor data to a control device of the medical apparatus 3. The collision sensor device 1 is formed by a flat layer structure. The core piece of the flat layer structure is a sensor structure formed by a first sensor layer 4 and a second sensor layer 5 that are separated by a spacer layer 6. A crumple layer 7 is provided between the sensor structure and the surface 2. The collision sensor device is closed with respect to the outside by a surface layer 8 that also laterally bounds the layer structure. Alternatively, the crumple layer 7 may be situated above the first sensor layer 4.

In this first example, the first sensor layer 4, the second sensor layer 5, and the spacer layer 6 form a sensor that operates according to the resistive sensor principle. For this purpose, the first sensor layer 4 and the second sensor layer 5 are in the form of at least partially conductive textile materials that are separated by the spacer layer 6. The spacer layer 6 is not conductive or is only poorly conductive (e.g., a spacer fabric). The conductive regions of the first sensor layer 4 and the second sensor layer 5 are arranged such that an item of location information is also obtained during reading. If a pressure is exerted on the surface of the collision sensor device 1, the spacer layer 6 is compressed. As a result, the first sensor layer 4 and the second sensor layer 5 come closer to one another or may touch one another, thereby resulting in a corresponding reduction in the resistance. Collisions may be thus detected. In other exemplary embodiments, the sensor structure may also form a capacitive or inductive sensor.

The crumple layer 7 is formed from foam and provides a defined run-on path for avoiding damage or injuries. The surface layer 8 is formed from a robust artificial leather or other suitable materials having a surface that may be disinfected.

All layers are textile layers or layers that may at least be processed by textile connecting methods. The layers may be connected by textile connecting methods (e.g., lamination and coating) such that the layers are adhesively connected.

Figure 2:
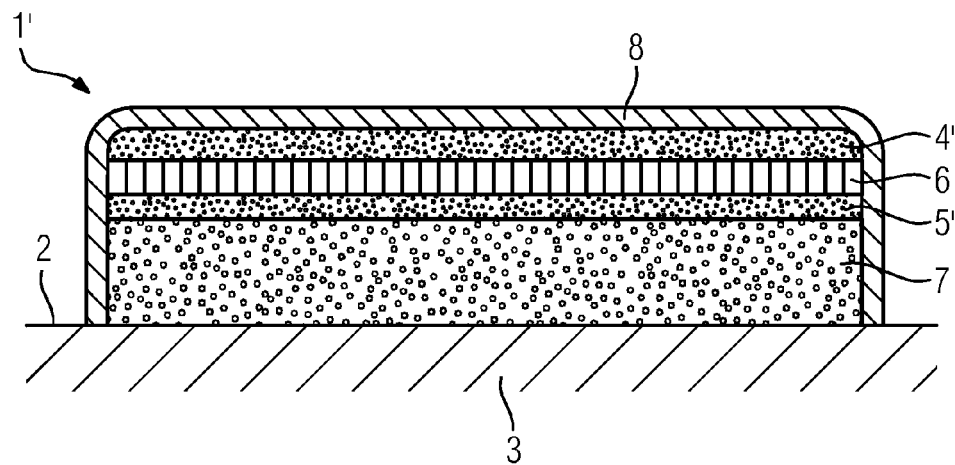
FIG. 2 shows a cross-sectional view of a second example of a collision sensor device.

FIG. 2 shows a cross-sectional view of a second embodiment of a collision sensor device 1' in accordance with the present teachings. The collision sensor device 1' is modified as compared to the collision sensor device 1 in FIG. 1 in that the each of the first sensor layer 4' and the second sensor layer 5' forms a separate sensor. As a result, two sensors that operate separately are formed in the sensor structure. In a measurement principle used for the first sensor layer 4' and the second sensor layer 5', an optical waveguide is used to radiate light into cavities that change size depending on the pressure acting on the collision sensor device 1', and the scattered light is measured. The sensors formed by the first sensor layer 4' and the second sensor layer 5' may also be configured for spatially resolved measurement.

In a variant of the second embodiment, the first sensor layer 4' and the second sensor layer 5' may implement sensors based on different measurement principles in order to provide a measuring redundancy. If appropriate, sublayers may be used in the sensor layers.

In this example, the spacer layer 6 provides a run-on path such that the different sensors are triggered in a temporally offset manner. As a result, different triggering stages may be achieved, as further explained in reference to FIG. 3.

Figure 3:
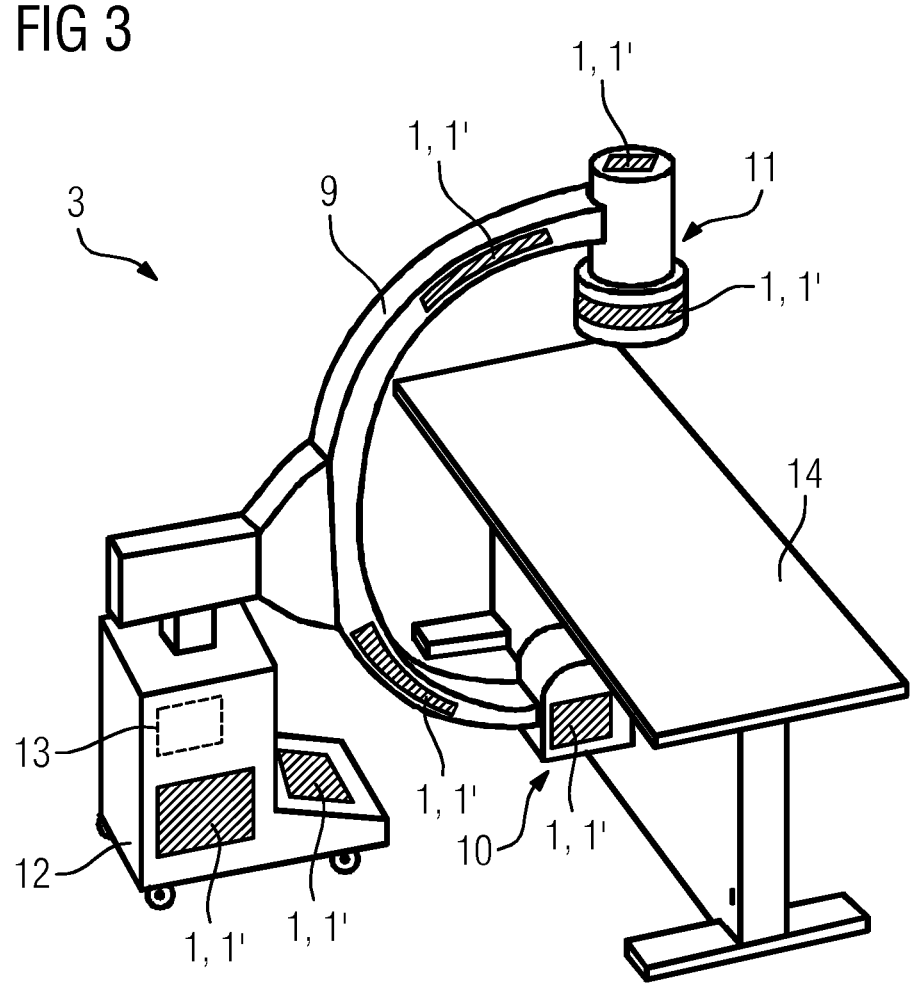
FIG. 3 shows a perspective view of an example of a medical apparatus.

FIG. 3 shows an example of a medical apparatus 3 in accordance with the present teachings. In the example, the medical apparatus 3 is in the form of an x-ray device with a C-arm 9 on which an x-ray emitter 10 and an x-ray detector 11 are arranged opposite one another. The C-arm 9 is carried by a stand 12 that may be moved using rollers. A control device 13 of the x-ray device may also be arranged in the stand 12. The control device 13 controls, inter alia, an automatic movement of the C-arm 9.

As shown in FIG. 3, a patient table 14 may be assigned to the medical apparatus 3 and a patient may be placed on the patient table 14 for examination.

Different types of collision may occur between components of the medical apparatus 3 and other objects (e.g., the patient table 4 and/or persons). Thus, a first collision sensor device 1 and a second collision sensor device 1' have been arranged at different locations on the medical apparatus 3 as a result of the flatness, ease of disinfectability, robustness, and run-on paths provided thereby. As a result, the first collision sensor device 1 and the second collision sensor device 1' also act as cushioning. The sensor data from the first collision sensor device 1 and the second collision sensor device 1' are received and evaluated by the control device 13. If the collision sensor devices are collision sensor devices 1' in accordance with the second embodiment having two sensors that respond in a temporally offset manner, two triggering stages are considered, respectively, in the control device 13.

In a first triggering stage (e.g., when only the collision sensor implemented by the outer sensor layer 4' responds), the movement of the component on which the collision sensor device 1' is arranged is slowed down and/or a first warning is output.

If the collision sensor implemented by the sensor layer 5' further away from the surface layer 8 also detects an event, there is a second triggering stage in which the movement of the affected component is entirely stopped and/or a further, stronger warning is output.

In addition, when using a collision sensor device 1' in accordance with the second embodiment, the control device 13 uses the data from the different sensors of the collision sensor device 1' as redundant data or data that check the plausibility of one another.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding claim—whether independent or dependent—and that such new combinations are to be understood as forming a part of the present specification.

The invention claimed is:

1. A collision sensor device for a medical apparatus, the collision sensor device comprising:
 a sensor structure comprising a first sensor and a second sensor, wherein the first sensor and the second sensor are separated by a spacer layer and are independently based on different operating principles and configured to provide separate measurement data;
 at least one crumple layer that adjoins one of the first sensor and the second sensor and is configured to provide a run-on path; and
 an outer surface layer configured to face away from the medical apparatus in an installed state of the collision sensor device;
  wherein the sensor structure, the at least one crumple layer, and the outer surface layer are configured as a multilayer structure.

2. The collision sensor device of claim 1, wherein at least one of the first sensor and the second sensor comprises a sub layer.

3. The collision sensor device of claim 1, wherein the first sensor and the second sensor are formed from a textile material.

4. The collision sensor device of claim 1, wherein the operating principles are independently selected from the group consisting of a capacitive sensor principle, a resistive sensor principle, an inductive sensor principle, a sensor principle based on light scattering in at least one cavity in the first sensor and the second sensor, and combinations thereof, wherein the at least one cavity has a variable size depending on a pressure acting on the collision sensor device.

5. The collision sensor device of claim 1, wherein the spacer layer is formed from a spacer fabric, a foam, or a spacer fabric and a foam.

6. The collision sensor device of claim 1, wherein a crumple layer of the at least one crumple layer adjoins the sensor structure on a side of the sensor structure that faces towards the medical apparatus in the installed state.

7. The collision sensor device of claim 1, wherein the at least one crumple layer comprises a spacer fabric, a foam, or a spacer fabric and a foam.

8. The collision sensor device of claim 1, wherein the outer surface layer comprises a material that is configured to be cleaned, disinfected, or cleaned and disinfected.

9. The collision sensor device of claim 1, wherein each of the first sensor, the second sensor, the spacer layer, the at least one crumple layer, and the outer surface layer is a textile layer, a layer configured to be processed by a textile connecting method, a layer configured to be adhesively connected, or combinations thereof.

10. A medical apparatus comprising at least one collision sensor device and a control device configured to evaluate sensor data from the at least one collision sensor device, wherein the at least one collision sensor device comprises:
 a sensor structure comprising a first sensor and a second sensor, wherein, the first sensor and the second sensor are separated by a spacer layer and are independently based on different operating principles and configured to provide separate measurement data;
 at least one crumple layer that adjoins one of the first sensor and the second sensor and is configured to provide a run-on path; and
 an outer surface layer configured to face away from the medical apparatus in an installed state of the collision sensor device;
  wherein the sensor structure, the at least one crumple layer, and the outer surface layer are configured as a multilayer structure.

11. The medical apparatus of claim 10, wherein the control device is configured to perform an operation selected from the group consisting of evaluating sensor data from whichever of the first sensor and the second sensor is closest to the outer surface layer with regard to a first triggering stage, evaluating sensor data from the other of the first sensor and the second sensor with regard to a second triggering stage, checking plausibility of the sensor data if different operating principles have been used, and combinations thereof.

12. The collision sensor device of claim 2, wherein the first sensor and the second sensor are formed from a textile material.

13. The collision sensor device of claim 2, wherein the spacer layer is formed from a spacer fabric, a foam, or a spacer fabric and a foam.

14. The collision sensor device of claim 3, wherein the spacer layer is formed from a spacer fabric, a foam, or a spacer fabric and a foam.

15. The collision sensor device of claim 4, wherein the spacer layer is formed from a spacer fabric, a foam, or a spacer fabric and a foam.

16. The collision sensor device of claim 2, wherein a crumple layer of the at least one crumple layer adjoins the sensor structure on a side of the sensor structure that faces towards the medical apparatus in the installed state.

17. The collision sensor device of claim 3, wherein a crumple layer of the at least one crumple layer adjoins the sensor structure on a side of the sensor structure that faces towards the medical apparatus in the installed, state.

18. The collision sensor device of claim 4, wherein a crumple layer of the at least one crumple layer adjoins the sensor structure on a side of the sensor structure that faces towards the medical apparatus in the installed state.

19. The collision sensor device of claim 8, wherein the material comprises artificial leather, has a thickness of 1 mm to 10 mm, or comprises artificial leather and has a thickness of 1 mm to 10 mm.

20. The collision sensor device of claim 9, wherein the textile connecting method comprises lamination, coating, or lamination and coating.

* * * * *